United States Patent [19]
Cornacchia et al.

[11] Patent Number: 5,472,403
[45] Date of Patent: Dec. 5, 1995

[54] DEVICE FOR AUTOMATIC INJECTION OF RADIONUCLIDE

[75] Inventors: Louis Cornacchia; John K. Alksne; George Ozaki, all of San Diego; David W. Yeung, Carlsbad, all of Calif.

[73] Assignee: The Regents of the University of California, Oakland, Calif.

[21] Appl. No.: 60,586

[22] Filed: May 11, 1993

[51] Int. Cl.$^6$ ..................................... A61M 5/00
[52] U.S. Cl. ............................... 600/4; 128/655
[58] Field of Search ................. 600/3, 4, 5; 128/653.4, 128/655; 604/92, 232, 246, 247, 284

[56] References Cited

U.S. PATENT DOCUMENTS

| | | | |
|---|---|---|---|
| 4,044,757 | 8/1977 | McWhorter et al. | 128/655 |
| 4,867,742 | 9/1989 | Calderon | 128/655 |
| 5,236,417 | 8/1993 | Wollis | 128/655 |
| 5,236,424 | 8/1993 | Imran | 804/93 |

*Primary Examiner*—Lee S. Cohen
*Assistant Examiner*—Brian M. Green
*Attorney, Agent, or Firm*—Brown, Martin, Haller & McClain

[57] ABSTRACT

The automatic injection device comprises two syringes, one for injecting a measured quantity of radionuclide and a second for injecting a saline solution for flushing the intravenous tubing through which the radionuclide has been delivered. Each of these syringes is driven by a motor which compresses the plunger of the syringe causing it to inject its contents. The motors receive an activation signal from a computer controller which initiates the injection sequence upon receipt of a trigger signal which is provided either by a separate seizure detection computer, by activation by the patient who recognizes an aura indicative of an imminent seizure, or by activation by medical personnel observing the patient. The computer implements a delay cycle to permit verification of the trigger to avoid initiating the injection sequence in the event of false alarms. Since the radionuclide is placed in the syringe in advance of the actual injection, decay of the radioactive element is compensated for by storing more radionuclide in the syringe than is needed, then calculating the quantity of radionuclide to be injected based upon the time delay from the filling of the syringe to the occurrence of the seizure and the half life of the radionuclide.

29 Claims, 3 Drawing Sheets

| SEIZURE CONFIRMED. PRESS NOW TO INJECT. | SEIZURE OBSERVED. PRESS BUTTON TO INITIATE INJECTION. |

_(page 1, column 1)_

DEVICE FOR AUTOMATIC INJECTION OF RADIONUCLIDE

FIELD OF THE INVENTION

The invention relates to single photon emission computed tomography (SPECT) and more specifically to a device for facilitating the use of SPECT for locating the site of a seizure in the brain.

BACKGROUND OF THE INVENTION

SPECT has been identified as a possible means for localization of seizure foci in epileptic patients. Recent studies (See, e.g. Rowe et al. "Visual and Quantitative Analysis of Interictal SPECT with Technetium-99 m-HM-PAO in Temporal Lobe Epilepsy", Journal of Nuclear Medicine 1991, 32:1688–1694.) have suggested that the time delay between seizure onset and radionuclide injection is a critical factor in determining both specificity and accuracy of the SPECT study. While an interictal SPECT is relatively easy to conduct when compared with an ictal SPECT, the former is found to be less accurate for localizing the ictal focus. However, a problem preventing a more widespread use of the ictal SPECT is that the duration of the post-ictal interval during which the injection of HMPAO-Tc$^{99}$ reveals hyperactivity is only about five minutes. Accurate localization of the focus is the most important step in surgical treatment of epilepsy, and must become part of the standard pre-operative patient evaluation. However, there are four obstacles which prevent the use of such a technique. First, the limitation in time between the seizure onset and radionuclide injection must be strictly observed. Second, quality control issues must be addressed and the handling of the radionuclide must be performed by qualified nuclear medicine personnel. Third, radiation safety guidelines must be observed since the radionuclide must be kept at the patient's bedside until a seizure occurs. Fourth, a technique must be readily incorporated into the standard hospital operating environment to avoid extensive training requirements.

In order to achieve the goals of an accurate SPECT technique without a specialized system, a nuclear medicine technologist would need to be at the patient's bedside at all times awaiting the occurrence of a seizure. This technologist would have to be trained in recognition of the onset of the seizure since the medication must be injected within four to five minutes of the seizure. If the injection occurs too soon or too late, the seizure focus may not be visualized.

SUMMARY OF THE INVENTION

It is an advantage of the present invention to provide a means for measuring relative brain blood flow with a spatial resolution of less than one centimeter and a temporal resolution on the order of minutes.

It is another advantage of the present invention to provide a means for freezing the pattern of cerebral blood flow at the moment of radionuclide injection.

Still another advantage of the present injection is to provide a means for capturing a SPECT image of the relative blood flow pattern in the brain at the time of a seizure.

Yet another advantage of the present invention is to provide an automatic means for injecting radionuclide within a few minutes of the onset of an epileptic seizure.

In an exemplary embodiment, the automatic injection device comprises two syringes, one for injecting a measured quantity of radionuclide and a second for injecting a saline solution for flushing the intravenous tubing through which the radionuclide has been delivered. Each of these syringes is driven by a DC motor which compresses the plunger of the syringe causing it to inject its contents. The DC motors receive an activation signal from a computer controller which initiates the injection sequence upon receipt of a trigger signal which is provided either by a separate seizure detection computer, by activation by the patient who recognizes an aura indicative of an imminent seizure, or by activation by medical personnel observing the patient. The computer implements a delay cycle to permit verification of the trigger to avoid initiating the injection sequence in the event of false alarms. Since the radionuclide is placed in the syringe in advance of the actual injection, decay of the radioactive element is compensated for by storing more radionuclide in the syringe than is needed, then calculating the quantity of radionuclide to be injected based upon the time delay from the filling of the syringe to the occurrence of the seizure and the half life of the radionuclide. After the correct amount of the radionuclide has been injected, the computer initiates a flush sequence which causes the saline solution within the second syringe to be injected through the intravenous tubing. A radiation shield is provided for surrounding the first syringe to minimize exposure of both patients and medical personnel to radiation.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF THE PREFERRED EMBODIMENT

Figure 1:
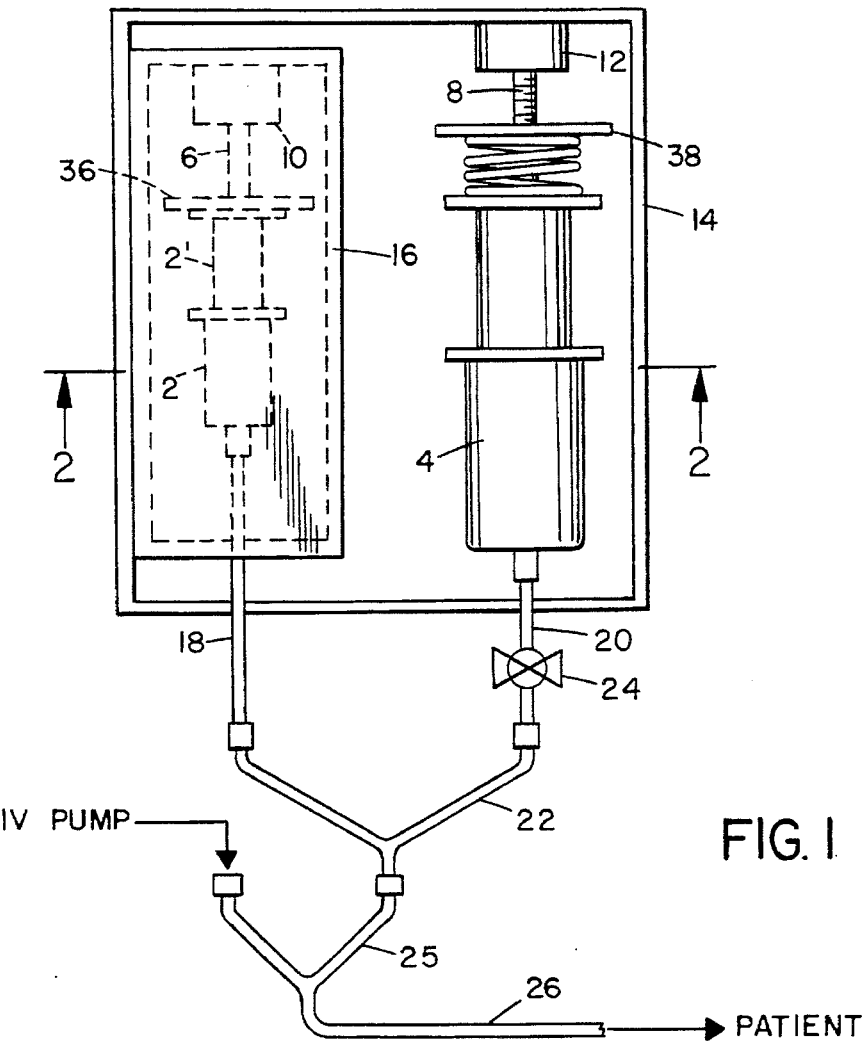
FIG. 1 is a diagrammatic top view of the device, with its top removed, illustrating its connection to the patient.
Figure 2:
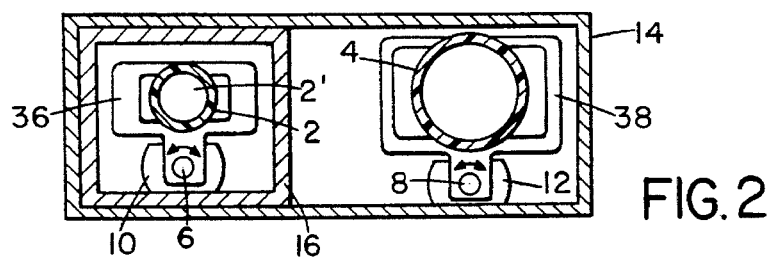
FIG. 2 is a cross-sectional view taken along line 2—2 of FIG. 1.

As illustrated in FIG. 1 and 2, the automatic radionuclide injection device comprises syringe injectors 2 and 4, drive shafts 6 and 8 and drive motors 10 and 12 enclosed in housing 14. Syringe 2 has a volume of 5 cc in which the radionuclide is contained. Syringe 2 is surrounded by lead shielding 16 to minimize exposure of the patient and medical personnel to radiation from the radionuclide and is connected at its outlet to intravenous extension tubing 18 and to "Y"-connector 22. Feeding the other side of "Y"-connector 22 is extension tubing 20 which is connected to syringe 4. Back flow inhibiting valves 24 may also be included in extension tubing 20 to avoid back leakage of radionuclide into the saline solution which is contained in syringe 4. "Y"-connector 22 can either act as an input to an optional second "Y"-connector 25, which allows an intravenous pump to be connected, or be connected directly into intravenous extension tubing 26, which is connected to the patient via a catheter.

Within housing 14, the two drive tracks 6 and 8 are associated with injectors 2 and 4, respectively, with a separate actuator arm providing connection between the respective drive tracks and syringes. The actuator arms 36 and 38 slide linearly along the length of the drive tracks, preventing motion in all other direction. The actuator arms come in direct contact with the syringe plungers and provide the mechanical force for depressing the plungers. Each drive track is directly coupled to the drive shaft of a DC downgeared reversible motor—motor 10 for syringe 2 or motor 12 for syringe 4. As an alternative to reversible DC motors, stepping motors or solenoid activators may be used to compress the syringes. Each drive screw is coupled to an actuator arm by a spindle. Turning the drive screw causes a spindle and, therefore, the actuator arm to move in one direction. For the large saline syringe 4, the drive shaft is connected to the actuator arm 38 by a spring so that the force transmitted to the syringe plunger is relatively constant during injection. The smaller forces involved in compressing plunger of syringe 2 permit more precise control by directly coupling the spindle to the actuator arm. Located on both sides of the actuator arm tracks are bars to which are mounted limiting switches 30 which provide feedback regarding the location of the actuator arms. The location of these switches can be adjusted to modify the range of motion of each actuator arm independently.

A 20K ohm linear potentiometer 32 is coupled to the actuator arm 36 for the radionuclide syringe 2. Potentiometer 32 provides data regarding the absolute position of the actuator arm 36. For economic reasons, the low degree of precision required for the saline flush generally does not warrant direct feedback of this nature for syringe 4, but such feedback may be included if desired.

Figure 3:
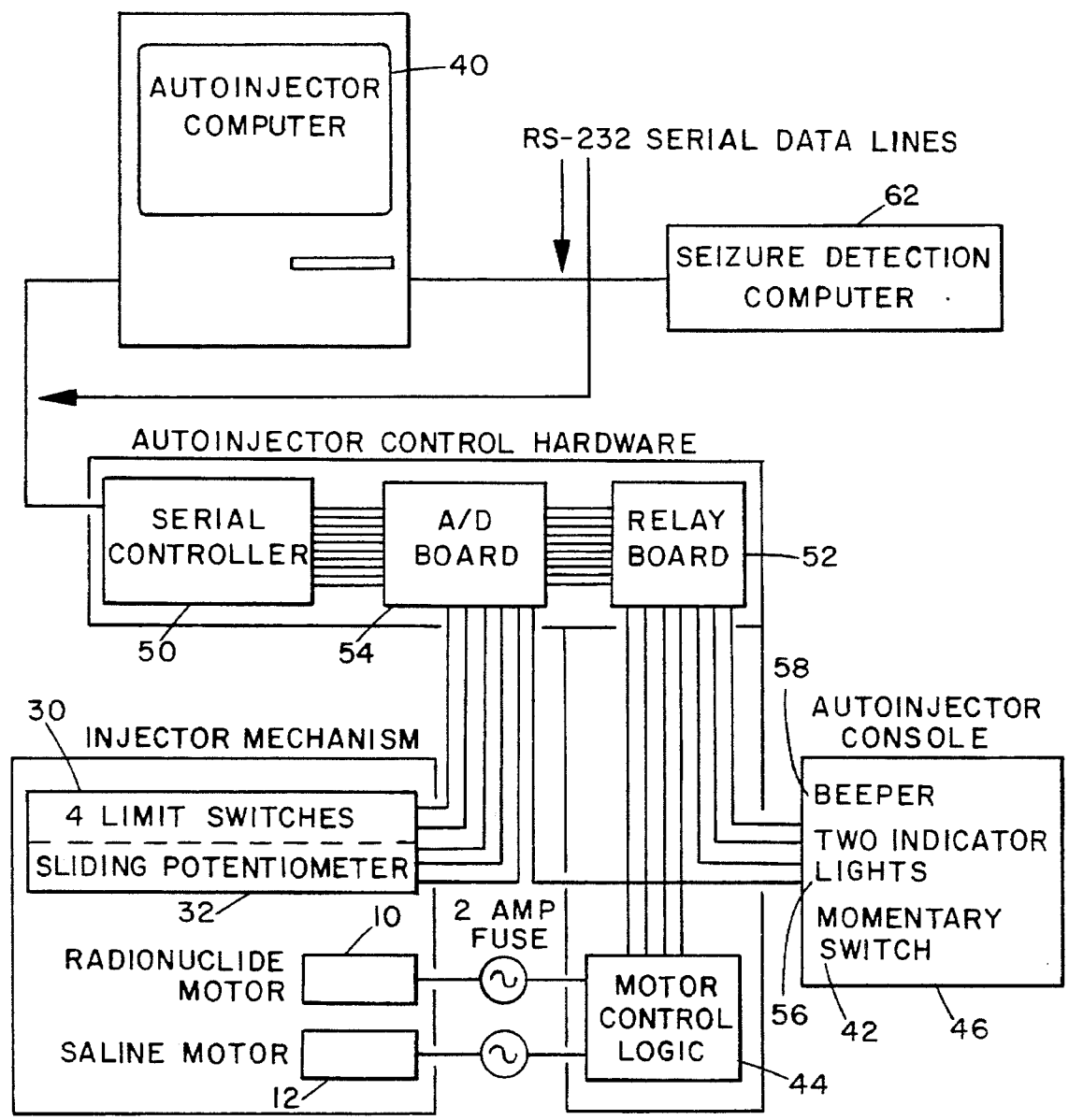
FIG. 3 is a schematic indicating the electrical connection within the device.

The wiring diagram for the auto injection device is provided in FIG. 3. A total of 11 conductors connects the auto injection device to the control box. These wires provide power for the DC motors, grounding for the chassis and signal data to or from the limit switches and potentiometer.

Lead shielding 16 is designed to reduce emitted radiation levels to less than 0.02 mRem an hour at a distance of one meter. The radionuclide remains shielded at all times, except during the 4 to 5 second period of injection, during which the radionuclide passes through the intravenous tubing to the patient. Tests performed on the auto injection device have shown that actual levels of radiation on the surface of the housing are almost always less than 0.02 mRem. Thus, most of the radiation measured on the surface of the auto injection unit's hood is attributable to background radiation present in the environment, which runs on the order of 0.01 to 0.02 m rem.

Loading the device involves the steps used in conventional injection of a radionuclide. Syringe 2, a sterile 5 cc syringe, is loaded with the radionuclide. Syringe 4, with a volume of 20 cc, is loaded with saline flush. These syringes are connected by "Y"-connector 22 to a long length of IV tubing 26. All IV tubing connections are secured by luer locks, as are know in the art. The syringes are then inserted into their respective bays within the auto injection device and locked in place. The auto injection device's door is closed, causing lead shielding 16 to surround the radionuclide syringe. Loading the auto injection device involves the same basic principles as performing a conventional injection with radionuclide, i.e., removing air bubbles, radio active materials handling techniques, etc.

The injection commences by activation of the radionuclide motor 10 which causes the radionuclide to be injected through the IV tubing and catheter. Back flow valves 24 prevent reflux of the radionuclide into the saline flush syringe 4. After injection of the radionuclide, the saline flush motor 12 causes the saline solution to be injected, flushing the remaining radionuclide from the tubing and into the patient. The IV tubing 26 is connected to the patient through a luer-locked intravenous catheter which allows easy disconnection from the device.

Once the injection occurs, the staff of an epilepsy monitoring unit informs the Nuclear Medicine Department who will then prepare the patient for scanning in the standard fashion.

The control hardware is connected computer 40 through an RS-232 serial interface which offers the ability to remotely locate the auto injection device control box from the controlling computer 40. This makes it possible to have one computer 40 controlling several auto injection devices simultaneously in a large epilepsy monitoring unit. The control box consists of three boards: 1) serial controller 50; 2) relay control card 52; and 3) an eight channel 8-bid analog to digital converter 54.

The main relays on board 32 control the indicator lights 56 and audible alarm 58 built into the control console. The main relays also drive four other relays (motor logic circuit 44) to provide independent reversible control of the DC motors 10 and 12. The A/D board 54 is connected to the switch 42 on the console to the four limiting switches in the auto injector, and the potentiometer 32 which provides positioning information for the radionuclide activator. Closing any of the limiting switches causes a 5 signal connected to separate channels on the A/D board to be grounded to zero.

Figure 4:
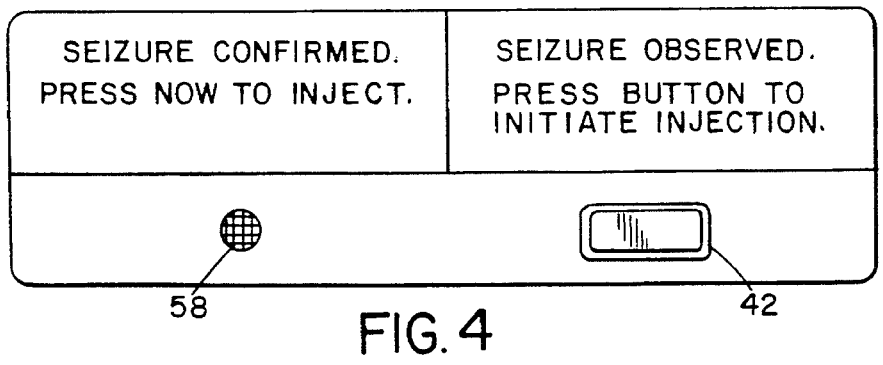
FIG. 4 is a diagram of the front panel of the preferred embodiment.

The interface between and the auto injection device is the console depicted in FIG. 4. The console 46 consists of a switch 42, two indicator lights 56 and an audible alarm 58. The indicator panels are each illuminated by two light bulbs connected in parallel to prevent bulb failure from disabling the system. The indicator light to the right labeled (SEIZURE OBSERVED—INITIATE INJECTION SEQUENCE), is limited when the system is first activated and before an event which initiates the injection sequence. The indicator blinks briefly once every 15 seconds to inform the user that the auto injection device is active. If the injection sequence is initiated in one of the ways listed below, the right indicator light labeled "INJECT NOW—SEIZURE CONFIRMED" is extinguished and the left indicator is activated with the audible alarm. When the left light is on and the audible alarm is on, the user knows that pressing the button 42 again will initiate the injection.

Figure 5:
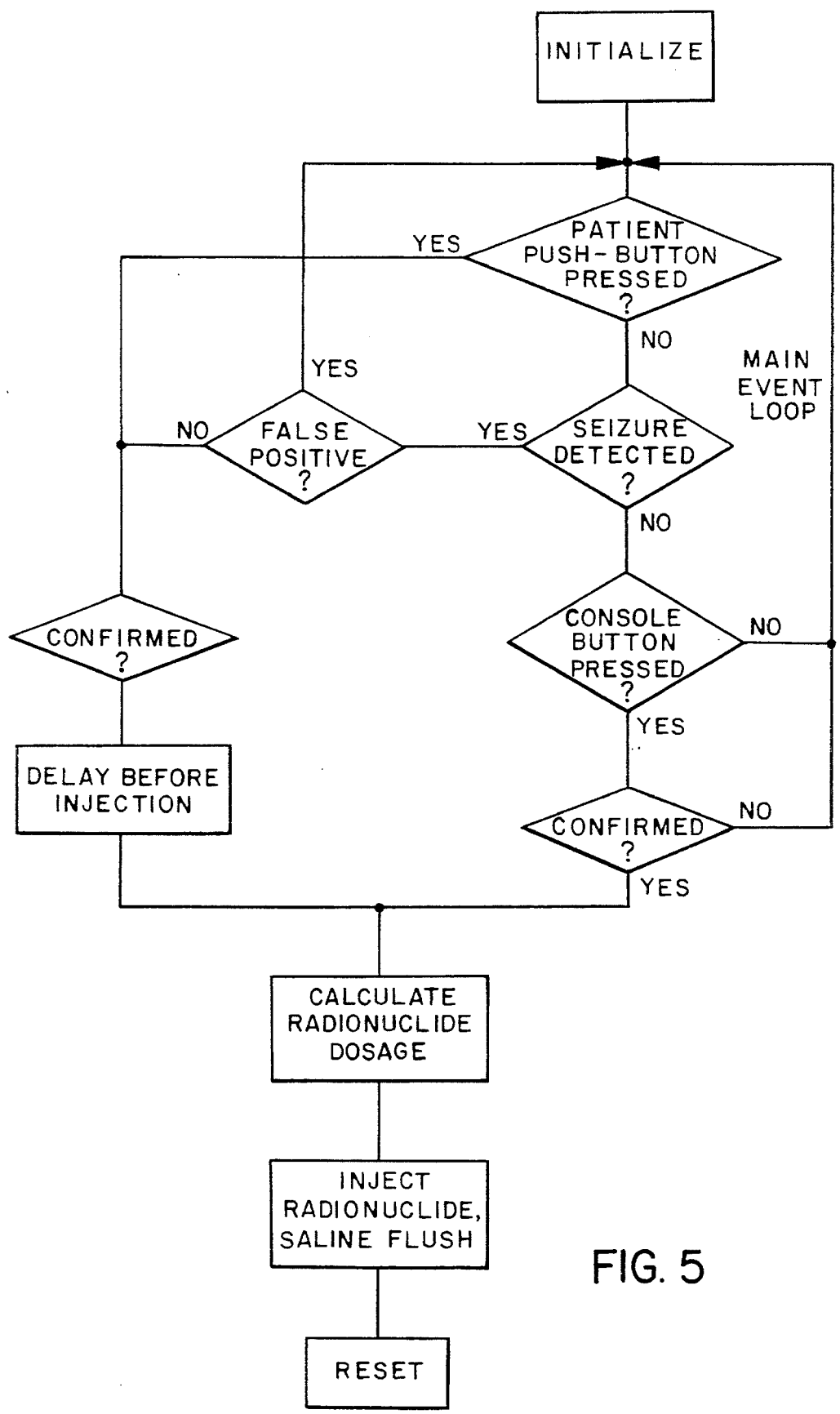
FIG. 5 is a flow diagram of the operation of the device of the present invention.

The computer 40 controls the auto injection device and receives information from the potentiometer and switches by means of a serial port in the back of the computer. Software flow chart appears in FIG. 5. The computer 40 has a second serial port 48 which is connected to the output of a second computer 62 which runs software. In the exemplary embodiment, this software is provided by Stellate Systems (BMSI). This is a commercially available seizure detection program based on software written Gene Gottmen. The seizure detection computer (SDC) 62 provides a heart beat signal through the serial port that conveys the time into three states: a) no event; b) a separate push-button has been pressed; and c) a seizure has been detected.

The auto injection computer 40 simultaneously monitors output from the seizure detection computer 62 and auto injector console 46. When the system is first activated it, initializes itself, calibrates the time on the two systems and waits to initiate the injection sequence. Three trigger events are possible: 1) the patient pushes a push button connected to the SDC 62; 2) the SDC 62 detects a seizure; or 3) EMU staff observe the symptoms of a seizure. The epilepsy monitoring unit staff can confirm the presence of a seizure thereby approve with injection of the radionuclide by pressing the button 42 on the auto injection device's console. If the injection sequence was initiated by a staff member, a staff member must press the button again after a brief refractory period to initiate the injection. This helps prevent accidental activation of the system. If the button is not pressed with 15 seconds, the audible alarm stops and the system begins scanning for another event.

The software employs a simple algorithm to minimize false positive activation of the auto injection device by a false positive event in the seizure detection computer 62. The MONITOR seizure detection software and others like it are designed to have a fairly high false positive rate to minimize the false negative rate. If every false seizure were to activate the auto injection, causing its alarm to go off, it would simultaneously annoy and desensitize the epilepsy monitoring unit staff. The auto injection device demands that the seizure detection computer 62 continues to detect a seizure for at least ten seconds with a minimum of four seconds of non-seizure detection before it initiates the injection sequence.

There is also a defined delay between the time of injection sequence initiation and the actual time of radionuclide injection when the injection sequence was initiated by the seizure detection computer or the patient. The reason for the built-in delay is that the patient can press the button at the time of seizure onset or during an aura and the seizure detection computer 62 can initiate the sequence early during the seizure. However, if the seizure is first detected by epilepsy monitoring unit staff on the basis of outward manifestation of the seizure, the seizure is probably already well under way and any further delay in injection would be undesirable. Thus, different delay periods are programmed depending on the trigger event. If the medical staff is present at the moment of onset of the seizure, the patient push button which is connected to the seizure detection computer 62 could be depressed to initiate the injection sequence. The medical staff would still need to press the button on the auto injection console to confirm the occurrence of a seizure.

The auto injection device varies the total volume of radionuclide injected to adjust for radioactive decay. The auto injector is loaded with approximately twice the standard dosage of radionuclide titrated to a total volume of 5 cc. The volume administered at any point after the system is loaded is calculated using the following formula:

$$V_f = (e^{-(ln2/t_{1/2})t})^{-1} V_0$$

where:

$V_f$=volume to inject after time t;

$V_o$=volume to inject at time zero;

t=elapsed time since session began; and $t_{1/2}$= half-life.

A full dose of radionuclide can be administered as which as six hours after initial preparation (half-life of Tc-99). At the time of injection, the software calculates the amount of radioactivity remaining in the radionuclide syringe and administers an amount sufficient to provide a full dose. For example, if the injection occurs immediately after preparation of the radionuclide, only 2.5 cc of the radionuclide will be administered. If the injection occurs three hours after preparation, 3.5 cc are administered. The total dose of radiation received by the patient is always constant. The accuracy of the hardware and software allows for 0.15±0.05 ml aliquots.

After injection, the auto injection device records all data to a hard disk file. This file contains information including the time of initiation of the monitoring session a record of the signals from the seizure detection computer 62, the time and mode of seizure detection, the time of confirmation and the time of injection. The file can be printed for a permanent record.

The operational status of the auto injection device can be determined quickly by examining the console 46. If the light in the right side is on and infrequently blinking, the system is active. If the light in the left side is on and audible alarm is sounding, the auto injector is armed and pressing the button 42 will cause the injection of the radionuclide. If both lights are on and the alarm is sounding, the radionuclide is being injected. If both lights are off, the auto injector is off. Not having separate status indicators increases reliability and decreases complexity. The information is present for those who require it, but it need not be understood for operation of the equipment. Referring to the flow chart on FIG. 5, the auto injection device first turns off all control relays and initialize the main event loop. While in the event loop, the system is said to be in a standby mode which is characterized by slow flashing of the "SEIZURE OBSERVED" indicator light. By causing the light to flash slowly, the user can assess that the computer is running the main loop and waiting for an event. Within the event loop, three conditions are tested: 1) does the ASCII stream from the seizure detection computer contain the code for an automatic seizure detection?; 2) does the ASCII stream from the seizure detection computer contain the code for a patient defined seizure event?; and 3) has any one pressed the trigger button 42 on the console 46?. If any of these are true, the software branches to the manual detection loop or to the automatic detection loop. If the trigger button 42 has been pressed or the seizure computer 62 communicated a patient defined seizure event, the system immediately enters alarm mode.

The alarm mode is characterized by the appearance of the "INJECT NOW" light and an audible alarm. In this mode, pressing the trigger button 42 causes a system to initiate an injection sequence. The only way to abort an injection sequence is to disconnect power from the system. If the trigger button is not pressed within a fixed number of seconds after entering this mode, the system aborts and returns to a standby mode. If the system entered alarm mode because the trigger button was pressed, there is a brief duration during which the system pauses before it begins testing for a repeat button press. Therefore, two rapid presses of the trigger button will not cause injection. This delay prevents accidental initiation of the injection sequence—the two consecutive button presses must be deliberate. The second button press must occur only after the system is in alarm mode ("INJECT NOW" light activated with alarm) for it to be confirmatory.

If the system enters the alarm mode through a patient defined seizure event, and the EMU staff member presses the trigger button, the system will delay the injection sequence for a pre-determined period. This delay period is a fixed number of seconds between the onset of a seizure aura and the actual start of injection. There is no delay if the system enters the alarm mode by detecting depression of the trigger button 42 as the triggering event.

If the system is in the main loop, i.e, standby mode, and it receives a signal from a seizure detection computer 62, it enters a level one alert, the system turns off the "SEIZURE OBSERVED" light and activates the "INJECT NOW" light, but it does not start emitting an audible alarm. Instead, it undergoes a predetermined delay to receive another seizure detection from the seizure detection computer. If this signal is received within the allotted time, the system enters a level two alert. If such a signal is not received within the allotted time, the system returns to standby mode. Pressing the trigger button 42 during a level one alert causes the system to enter alarm mode, during which it will wait for confirmation prior to initiating the injection sequence.

Level two alert is equivalent to the alarm mode in that pressing the trigger button 42 will initiate the injection sequence after a fixed delay. If the trigger button is not pressed and the system does not receive additional automatic seizure detection messages from the seizure detection computer 62 within a fixed period of time, the system reverts to the standby mode. If the seizure detection computer 62 continues to convey that it is detecting a seizure, then the auto injection device enters a level three alert.

A level three alert is equivalent to a level two alert, except that the system will wait a longer period of time for a trigger button press prior to returning to a standby mode. The purpose of this additional level is to allow the system to be aborted more rapidly if the seizure detection computer 62 only briefly detected seizure activity. Most seizure detection software generates a large number false positive detections. If the seizure detection computer 62 repeatedly reports the presence of a seizure over a period of 10 to 15 seconds, it is much more likely that the event is an actual seizure.

The injection sequence begins with a delay if the system was signaled by a patient defined seizure event or by pressing the trigger button. The delay period is different for each of these two conditions. Once the delay is overcome and the system begins incrementally compressing the radionuclide syringe plunger 2'.

Movement of the actuator arms 36 and 38 in both directions involves the same basic process. The software moves the actuator arm a short distance by activating the appropriate motor for a brief period. The polarity of the applied signal determines the direction of movement. After this brief movement, the software tests the appropriate limiter switch. If this switch is open, the process is repeated. If this switch is closed, the actuator arm has been fully retracted or advanced. The system first advances the radionuclide syringe plunger 2 then advances the saline flush syringe plunger 4. The radionuclide syringe plunger 2 is retracted after which the saline solution plunger 4 is retracted. When this sequence is completed, the system shuts down the computer in preparation for the system to be unplugged so the patient can been taken for a SPECT scan.

Table 1 below system status chart indicating the status of the various indicators on the console under certain events.

TABLE 1

| Description | Seizure Observed | Inject Now | Alarm |
| --- | --- | --- | --- |
| System Initialization | on | on | on |
| Standby Mode | on | off | off |
| Alarm Mode | off | on | on |
| Alert Level 1 | off | on | off |
| Alert Level 2 | off | on | on |
| Alert Level 2 | off | on | on |
| Injection Mode | on | on | off |
| Ready to be Unplugged | off | off | off |

The device of the present invention makes routine ictal SPECT scanning possible by automated radionuclide injection, making seizure locus mapping an achievable goal and valuable tool for treatment of patients with intractable epilepsy. The inventive device can be activated by a seizure detection computer, by the patient or by EMU staff, but the injection requires confirmation of a seizure by trained health care personnel. This system compensates for time delays in loading of the radionuclide, thus frees up medical personnel who might otherwise be required to remain with the epilepsy patient constantly until a seizure occurs in order to make the ictal SPECT scan possible.

It will be evident that there are additional embodiments which are not illustrated above but which are clearly within the scope and spirit of the present invention. The above description and drawings are therefore intended to be exemplary only and the scope of the invention is to be limited solely by the appended claims.

We claim:

1. A device for facilitating use of ictal single photon emission computed tomography for localizing seizure focus in a patient comprising:

a first syringe for retaining a first quantity of a radionuclide;

a first activation means for causing said first syringe to inject said radionuclide;

a second syringe for injecting a saline solution;

a second activation means for causing said second syringe to inject said saline solution;

tubing for delivering fluids to said patient intravenously;

a "Y" connector having a first input and a second input connected to said first syringe and said second syringe respectively and an output connected to said tubing for directing said radionuclide and said saline solution into said tubing;

a plurality of trigger means, each trigger means for providing a trigger signal indicative of occurrence of a seizure; and a computer means for receiving said trigger signal, introducing a verification delay for verifying said occurrence of a seizure, calculating a second quantity of said radionuclide less than or equal to said first quantity of said radionuclide based upon a time delay between a filling of said first syringe and said occurrence of a seizure and a half-life of said radionuclide, providing an inject signal to said first activation means to inject said second quantity and providing a flush signal to said second activation means to inject said saline solution to flush said tubing;

wherein said radionuclide is injected within a critical period following said occurrence of a seizure to permit localization of the seizure focus in said patient's brain using ictal single photon emission computed tomography.

2. A device as in claim 1 further comprising:

verification means for verifying said occurrence of a seizure during said verification delay; and reset means for returning said device to a standby mode if no verification occurs.

3. A device as in claim 1 wherein each said trigger means is a seizure detection computer.

4. A device as in claim 1 wherein each said trigger means is a patient-activated input means said patient-activated input means being manually activated by the patient in response to detecting an onset of the seizure.

5. A device as in claim 1 wherein each said trigger means is a medical observer activated input means, said medical observer activated input means being manually activated by a medical staff member upon observance of an onset of said seizure.

6. A device as in claim 1 wherein said first activation means comprises a DC motor.

7. A device as in claim 1 wherein said second activation means comprises a DC motor.

8. A device as in claim 1 wherein said first activation means comprises a stepper motor.

9. A device as in claim 1 wherein said second activation means comprises a stepper motor.

10. A device as in claim 1 wherein said first activation means comprises a solenoid.

11. A device as in claim 1 wherein said second activation means comprises a solenoid.

12. A device as in claim 1 further comprising a radiation shield surrounding said first syringe.

13. A device as in claim 1 wherein said computer means varies said verification delay in accordance with which of said plurality of trigger means provides said trigger signal.

14. A device as in claim 1 wherein said computer means further comprises memory means for maintaining a record of said occurrence of a seizure and said second quantity.

15. A device as in claim 14 further comprising output means for providing a hard copy of said record.

16. A device as in claim 1 further comprising an alarm device connected to each said trigger means for emitting an audible alarm in response to said trigger signal.

17. An apparatus for automatically injecting a radionuclide into a patient in response to an epileptic seizure, said apparatus comprising:

a first syringe for retaining a first quantity of a radionuclide;

a first activation means for causing said first syringe to inject said radionuclide;

a second syringe for injecting a saline solution;

a second activation means for causing said second syringe to inject said saline solution;

tubing connected to each of said first syringe and said second syringe for delivering fluids from each said syringe to said patient intravenously;

at least one trigger means for providing a trigger signal indicative of occurrence of a seizure; and a computer means for receiving said trigger signal, introducing a verification delay for verifying said occurrence of a seizure, calculating a second quantity of said radionuclide less than or equal to said first quantity based upon a time delay between a filling of said first syringe and said occurrence of a seizure and a half-life of radionuclide, providing an inject signal to said first activation means to inject said second quantity and providing a flush signal to said second activation means to inject said saline solution to flush said tubing.

18. An apparatus as in claim 17 further comprising:

verification means for verifying said occurrence of a seizure during said verification delay; and reset means for returning said device to a standby mode if no verification occurs.

19. An apparatus as in claim 17 wherein said computer means varies said verification delay is varied according to in accordance with which of said plurality of trigger means provides said trigger signal.

20. An apparatus as in claim 17 wherein said at least one trigger means is a seizure detection computer.

21. An apparatus as in claim 17 wherein said at least one trigger means is a patient-activated input means, said patient-activated input means being manually activated by said patient in response to detection of an onset of the seizure.

22. An apparatus as in claim 17 wherein said at least one trigger means is a medical observer activated input means, said medical observer activated input means being manually activated by a medical staff member upon observance of an onset of the seizure.

23. An apparatus as in claim 17 wherein said first activation means comprises a DC motor.

24. An apparatus as in claim 17 wherein said second activation means comprises a DC motor.

25. An apparatus as in claim 17 further comprising an alarm device in electrical connection with said at least one means for emitting an audible alarm in response to said trigger signal.

26. An apparatus as in claim 17 further compromising a radiation shield surrounding said first syringe.

27. A device for injection of a radionuclide having a half-life to facilitate mapping of a cerebral blood flow pattern in a patient upon detection of a seizure, the device comprising:

a plurality of syringes, a first syringe of said plurality containing a first quantity of said radionuclide;

an electronically-controlled activation means corresponding to each syringe of said plurality of syringes for causing said each syringe to inject its contents;

intravenous tubing having at least one first end connected to each of said plurality of syringes and a second end having a catheter attached thereto for insertion into the patient;

a plurality of trigger means, each trigger means for generating a trigger signal in response to detection of the seizure;

a computer controller connected to said plurality of trigger means for initiating an injection sequence in response to receiving said trigger signal, said injection sequence including calculating a second quantity of the radionuclide less than or equal to said first quantity said based upon the half-life of the radionuclide and a time delay between loading of the radionuclide into said first syringe and detection of the seizure, and generating an electrical signal for activating said activation means corresponding to said first syringe for injecting said second quantity.

28. A device as in claim 27 wherein said computer controller introduces a verification delay into the injection sequence after receiving said trigger signal and further comprising a verification means for verifying detection of the seizure and providing a confirmation signal to said computer controller to continue the injection sequence.

29. A device as in claim 27 wherein said computer controller generates a flush signal following injection of said second quantity whereby a saline solution is injected through said intravenous tubing by a second syringe of said plurality of syringes.

\* \* \* \* \*

UNITED STATES PATENT AND TRADEMARK OFFICE
CERTIFICATE OF CORRECTION

PATENT NO. : 5,472,403
DATED : DECEMBER 5, 1995
INVENTOR(S) : LOUIS CORNACCHIA, JOHN K. ALKSNE, GEORGE OZAKI AND DAVID W. YEUNG

It is certified that error appears in the above-indentified patent and that said Letters Patent is hereby corrected as shown below:

- COLUMN 9, CLAIM 19, LINE 62, DELETE "IS VARIED ACCORDING TO" AND

- COLUMN 10, CLAIM 25, LINE 19, BEFORE "MEANS" INSERT --TRIGGER--.

Signed and Sealed this

Thirtieth Day of April, 1996

Attest:

BRUCE LEHMAN

*Attesting Officer*   *Commissioner of Patents and Trademarks*